United States Patent [19]
Braun et al.

[11] Patent Number: 5,569,782
[45] Date of Patent: Oct. 29, 1996

[54] PROCESS FOR PREPARING POLYFLUOROCHLOROCARBONYL CHLORIDES AND PERFLUOROCARBONYL CHLORIDES WITH ADDITION OF CHLORINE

[75] Inventors: Max Braun, Wedemark; Werner Rudolph, Hanover; Kerstin Eichholz, Langenhagen, all of Germany

[73] Assignee: Solvay Fluor und Derivate GmbH, Hanover, Germany

[21] Appl. No.: 360,026

[22] Filed: Dec. 20, 1994

[30] Foreign Application Priority Data

Dec. 23, 1993 [DE] Germany .............. 43 44 241.2
Jun. 15, 1994 [DE] Germany .............. 44 20 763.8

[51] Int. Cl.⁶ ............................................. C07C 51/58
[52] U.S. Cl. .................... 562/863; 562/851; 562/852; 204/157.87; 204/157.94; 204/158.11
[58] Field of Search ............................... 562/863, 852, 562/851

[56] References Cited

U.S. PATENT DOCUMENTS

| | | | |
|---|---|---|---|
| Re. 29,044 | 11/1976 | Konno et al. | 204/163 R |
| 3,151,051 | 7/1964 | Braid et al. | 204/158 |
| 3,446,721 | 5/1969 | Scherer et al. | 204/158 |
| 3,725,475 | 4/1973 | Paucksch et al. | |
| 3,883,407 | 5/1975 | Dittman et al. | |
| 4,701,563 | 10/1987 | Franke et al. | |
| 5,259,938 | 11/1993 | Huang | 204/157.87 |

FOREIGN PATENT DOCUMENTS

| | | |
|---|---|---|
| 1069137 | 11/1959 | Germany . |
| 4227130 | 2/1994 | Germany . |
| WO94/06744 | 3/1994 | WIPO . |
| WO94/06742 | 3/1994 | WIPO . |

OTHER PUBLICATIONS

Haszeldine et al., "Oxidation of Polyhalogeno–compounds . . . ", Journal 1959, pp. 387–396.
Francis et al., "Oxidation of Polyhalogeno–compounds . . . ", Journal (1955), pp. 2151–2163.
Wheaton et al., "Methyl Chlorodifluoroacetate as . . . ", J. Fluorine Chem., vol. 8, pp. 97–100 (1976).
Edney et al., "Chlorine Initiated Oxidation . . . ", J. Atmospheric Chem., vol. 12, pp. 105–120 (1991).

Primary Examiner—Paul J. Killos
Assistant Examiner—Dwayne C. Jones
Attorney, Agent, or Firm—Evenson, McKeown, Edwards & Lenahan, P.L.L.C.

[57] ABSTRACT

A process for preparing polyfluorochloro- and perfluorocarbonyl chlorides, for example for preparing perfluoropropionyl chloride, chlorodifluoroacetyl chloride or trifluoroacetyl chloride, in which starting materials are employed which have a $CHCl_2$ group which is converted to a $C(O)Cl$ group by photochemical oxidation with oxygen in the presence of added elemental chlorine and under exposure to activating irradiation by light having a wavelength $\lambda \geq 290$ nm. The procedure is preferably unpressurized. Outstanding conversions with high selectivity are achieved using doped Hg light sources.

14 Claims, No Drawings

PROCESS FOR PREPARING POLYFLUOROCHLOROCARBONYL CHLORIDES AND PERFLUOROCARBONYL CHLORIDES WITH ADDITION OF CHLORINE

BACKGROUND OF THE INVENTION

The invention relates to a process for preparing polyfluorochloro- and perfluorocarbonyl chlorides, in particular to a process for preparing trifluoroacetyl chloride, chlorodifluoroacetyl chloride and perfluoropropionyl chloride, in the presence of added elemental chlorine.

Polyfluorochlorocarbonyl chlorides and perfluorocarbonyl chlorides are intermediates in chemical synthesis, e.g. in the preparation of pharmaceuticals and agrichemicals.

Chlorodifluoroacetyl chloride is an intermediate which can be used in various ways in chemical synthesis, for example in preparing dyestuffs. Alkyl and aryl halides can be trifluoromethylated in the presence of potassium fluoride and copper iodide by a derivative of chlorodifluoroacetyl chloride, namely by the methyl ester. Until now, chlorodifluoroacetyl chloride has been prepared by solvolysis of $CF_2ClCCl_3$ with oleum or $SO_B$ in the presence of mercury compounds and sulfur oxychlorides, as described in U.S. Pat. No. 3,725,475. The aforementioned methyl ester is also a precursor for preparing difluorocarbene; see G. A. Wheaton and D. J. Donald in *J. Fluorine Chem.*, Vol. 8, pages 97–100 (1976). Difluorocarbene is used in preparing insecticides; see U.S. Pat. No. 4,701,563 (= EP 198,791). The preparation of difluorocarbene from trifluoromethylphenyl mercury and other compounds of this type is problematical from the environmental point of view.

Trifluoroacetyl chloride is also an important intermediate in chemical synthesis. The reaction with trifluoroethanol leads to the corresponding ester, which can be cleaved by hydrogenation into two molecules of trifluoroethanol. Trifluoroethanol is a solvent which can also be employed in drying and cleaning processes.

Perfluoropropionyl chloride is an intermediate in chemical synthesis. It can be hydrogenated to give 2,2,3,3,3-pentafluoropropanol, which when mixed with 1-chloro-2,2,2-trifluoroethyl difluoroethyl ether is suitable as a cooling lubricant or in cleaning and drying processes, see Published German Patent Application No. DE-OS 4,227,130.

SUMMARY OF THE INVENTION

It is the object of the present invention to provide a process for preparing polyfluorochlorocarbonyl chlorides and perfluorocarbonyl chlorides, in particular for preparing trifluoroacetyl chloride, chlorodifluoroacetyl chloride and perfluoropropionyl chloride, which can be carried out without addition of mercury compounds and which affords high yields with high selectivity and high reaction rates.

This and other objects of the invention are achieved by providing a process for preparing a compound corresponding to the formula $RCFXC(O)Cl$ in which R is fluorine or perfluorinated alkyl having 1 to 10 carbon atoms and X is chlorine or fluorine, said process comprising reacting a starting compound corresponding to the formula $RCFXCHCl_2$ in which R and X have the above meanings, with oxygen in the gas phase in the presence of added elemental chlorine and under exposure to activating irradiation with light having a wavelength $\lambda \geq 290$ nm.

DETAILED DESCRIPTION OF PREFERRED EMBODIMENTS

In the process according to the invention for preparing compounds of the formula $RCFXC(O)Cl$, in which R is fluorine or perfluorinated alkyl having 1 to 10 carbon atoms and X is chlorine or fluorine, compounds of the formula $RCFXCHCl_2$, in which R and X have the aforementioned meanings, are reacted with oxygen in the gas phase in the presence of added elemental chlorine and under exposure to activating irradiation by light having a wavelength $\lambda \geq 290$ nm. R is preferably fluorine, $CClF_2$ or perfluorinated C1–C3-alkyl. It is particularly preferred for R to represent fluorine, $CClF_2$ or perfluorinated methyl or perfluorinated ethyl.

As the source of activating irradiation one can use, for example, irradiation lamps (e.g. Philips fluorescent tubes) which emit only (UV) light having a wavelength of over 290 nm ($\lambda \geq 290$ nm). In such a case it is possible to irradiate through quartz glass. The only prerequisite for this variant is that these lamps emit in the absorption range of elemental chlorine.

Alternatively one can use, for example, irradiation lamps (e.g. Hg medium- or high-pressure lamps) which also emit lines in the wavelength range below 290 nm ($\lambda < 290$ nm). In this variant, it is necessary to irradiate through a glass which is transparent only for light of 290 nm or above ($\lambda \geq 290$ nm), i.e. a glass which filters out the shorter-wave portion of the radiation having wavelengths $\lambda$ of $< 290$ nm. Borosilicate glasses, for example, are highly suitable for this. Glasses of this type customarily contain 7 to 13% of $B_2O_3$, 70 to 80% of $SiO_2$, and also 2 to 7% of $Al_2O_3$ and 4 to 8% of $Na_2O+K_2O$ as well as 0 to 5% of alkaline earth metal oxides. Known trademarks for borosilicate glasses include Duran, Pyrex and Solidex.

Naturally, it is also possible to use a procedure in which employs an irradiation lamp which radiates light above the wavelength indicated, and additionally uses glasses which are transparent to light above the wavelength indicated (i.e. are correspondingly opaque to light below the wavelength indicated).

Suitable sources of irradiation also include high-pressure mercury lamps which, due to the presence of a doping agent, radiate primarily or exclusively in the wavelength range at or above 290 nm. High-pressure mercury lamps, for example, have a very intensive band in the range of 254 nm which, as has been described above, is filtered out, e.g. by borosilicate glass. In Hg high-pressure lamps doped by metal iodides, this line is strongly suppressed. The frequently more than proportional increase in the conversion rate using doped light sources of this type is surprising. Outstanding results with respect to the conversion rate and selectivity are achieved with Hg high-pressure lamps which are doped with gallium iodide, and particularly with lamps which are doped with thallium iodide or cadmium iodide. However, even when using such light sources, it is advantageous to use glass which filters out the shorter-wave radiation portion of $\lambda < 290$ nm.

It is advantageous to carry out the reaction at a reaction temperature and pressure at which no condensation occurs on the apparatus components. Desirably, the reaction is carried out at a temperature of up to 200° C., preferably at a temperature in the range from 50° to 130° C. The reaction can be carried out at reduced pressure, but preferably it is carried out at a pressure of 1 to 10 atm (abs.). It is especially preferred to carry out the reaction under "unpressurized" conditions. As used herein, the term "unpressurized" means that no additional pressure acts on the reaction mixture beyond the ambient pressure (i.e. about 1 atm), the supply pressure of the oxygen gas (or oxygen-containing gas; e.g. air can be employed) and of the chlorine, and the pressure which may be generated as a result of formation of hydrogen chloride gas in the reaction.

The process can be carried out batchwise or continuously, the reaction advantageously being carried out in a flow-through apparatus. Preferably, a procedure is used in which starting materials (i.e. the appropriate hydrogen- and halogen-containing starting compound, chlorine and oxygen) are continuously introduced into the flow-through apparatus, and reaction product is continuously withdrawn in an amount corresponding to the amount of starting material introduced.

The molar ratio between the starting compound RCFX-$CHCl_2$ and the elemental chlorine can vary over a wide range, e.g. from 100:1 to 1:1. Particularly good results are achieved if the molar ratio between the starting compound and the elemental chlorine is in the range from 100:1 to 3:1, preferably 50:1 to 5:1.

The molar ratio between the starting compound RCFX-$CHCl_2$ and oxygen can also vary over a wide range. Advantageously, at least 0.5 mole of oxygen are used per mole of starting compound. Particularly good results are achieved if the molar ratio between the starting compound and the oxygen is in the range from 1:0.5 to 1:20, especially 1:1.1 to 1:3. The oxygen can be employed in the form of air or as a mixture of $O_2$ and inert gas, but preferably substantially pure oxygen is used.

The required starting materials corresponding to the formula $RCFXCHCl_2$ are known or can be prepared by standard methods. The preparation of 1,1,1,2,2-pentafluoro-3,3-dichloropropane (HCFC 225 ca) from 1,1,1,2,2-pentafluoro-3,3,3-trichloropropane and hydrogen with iridium catalysts is described, for example, in Published Japanese Patent Application No. JP-A 4-210,653. This HCFC 225ca is then processed further by the process of the invention to give perfluoropropionyl chloride.

A particularly preferred embodiment relates to the preparing of trifluoroacetyl chloride, chlorodifluoroacetyl chloride and perfluoropropionyl chloride.

This preferred embodiment comprises preparing compounds of the general formula $CF_2XC(O)Cl$, in which X=$CF_3$, Cl or F, and is characterized in that HCFC 225ca, 1,1-difluoro-1,2,2-trichloroethane (HCFC 122) or 1,1,1-trifluoro-2,2-dichloroethane (HCFC 123) is reacted with oxygen in the gas phase in the presence of added elemental chlorine and under irradiation by light having a wavelength $\lambda \geq 290$ nm. The invention will be described in further detail hereinafter with reference to this illustrative preferred embodiment.

The activating irradiation is preferably carried out using light sources which emit light which is at least partially in the UV range. For example, high-pressure and medium-pressure mercury lamps are suitable. Fluorescent tubes can also be used, e.g. Philips fluorescent tubes with selective emission at 350 nm. UV-transparent material is recommended as a material for the corresponding apparatus components. As noted above, quartz can be used if the light sources emit light above a wavelength of 290 nm. Otherwise or alternatively, the aforementioned borosilicate glasses are used.

With regard to product purity, it is desirable that as little water as possible be present in the reaction. If desired, the reactants can be freed of entrained water in a known manner, for example by contact with drying agents such as drying beads, phosphorus pentoxide or highly concentrated sulfuric acid.

The average residence time in the reaction vessel is preferably between 0.1 and 30 minutes. The optimum average residence time, which depends, inter alia, on the power of the lamp and on the geometric parameters of the irradiation apparatus (flow-through apparatus), can be determined by simple manual tests and analysis of the product stream, e.g. by gas chromatography.

Better conversion rates and higher selectivity can be achieved if, instead of a single irradiation lamp of specific power, two or more lower-powered lamps of the same total power are used in a succession of reactors. A good swirling of the reaction mixture, e.g. by means of suitable fittings built into the reactor, is also often advantageous.

The process offers some surprising advantages. For example, if borosilicate glass is used, this is not attacked or is at most attacked to an extremely small extent by aggressive reaction products. The high conversion rate with high selectivity is also surprising despite the required use of elemental chlorine (no or only traces of chlorinated by-products are found), particularly when using high-pressure mercury light sources doped with metal iodide.

Edney et al., *J. Atmos. Chem.*, Vol. 12, No. (2), pp. 105–120 (1991) reports a scientific investigation in which the oxidation of HCFC 123 in the presence of chlorine was investigated by a Fourier Transform IR method. The investigation was carried out at reduced (subatmospheric) pressure in an IR measuring cell which coincidentally was made of Pyrex glass. However, only the investigations by the inventors of the present application led to the discovery that irradiation with light having a wavelength $\lambda \geq 290$ nm, especially when using doped light sources, specifically makes possible the technically advantageous targeted use of such a process for preparing specific carbonyl chlorides with high selectivity and yield.

The following examples are intended to illustrate the invention in further detail without restricting its scope (Example 1 is a comparison example; the other examples are according to the invention).

Example 1: (Comparison example) Continuous preparation of chlorodifluoroacetyl chloride by photochemical oxidation of $CF_2Cl$—$CHCl_2$ (HCFC 122) with oxygen through quartz glass and with chlorine as a sensitizer.

A mixture of $CF_2Cl$—$CHCl_2$ (from a pre-evaporator at T=150° C.) and pure oxygen in the molar ratio 1:1.4 was metered as a gas together with 10 mole-% of $Cl_2$ (based on HCFC 122) at an internal reactor temperature of 100° C. into a 400 ml immersed shaft photolysis reactor and simultaneously irradiated through quartz glass using a high-pressure mercury light source TQ 718 from Heraeus (500 W setting). The rate of addition of HCFC 122 was 0.91 mole/30 min. The gas stream leaving the reactor contained 72.4% of chlorodifluoroacetyl chloride and 4.7% of 1,1-difluorotetrachloroethane (112a) as products. The conversion of the HCFC 122 amounted to 99% and the selectivity was 72%.

Example 2: Continuous preparation of chlorodifluoroacetyl chloride by photochemical oxidation of $CF_2Cl$—$CHCl_2$ (HCFC 122) with oxygen through borosilicate glass and with chlorine as a sensitizer.

A mixture of $CF_2Cl\text{—}CHCl_2$ (HCFC 122; from a pre-evaporator at T= 150° C.) and pure oxygen in a molar ratio of 1:1.4 was metered as a gas together with 10 mole-% of $Cl_2$ (based on HCFC 122) at an internal reactor temperature of 100° C. into a 400 ml immersed shaft photolysis reactor and simultaneously irradiated through Pyrex™ glass using a high-pressure mercury light source TQ 718 from Heraeus (700 W setting). The rate of addition of HCFC 122 was 0.91 mole/30 min. The gas stream leaving the reactor contained as products: 93.0% of chlorodifluoroacetyl chloride in addition to 0.3% of 1,1-difluorotetrachloroethane (112a). The conversion of HCFC 122 was 69% and the selectivity 93%.

Example 3

The reaction mixture and procedure corresponded to Example 2, except that 24 mole-% of chlorine gas (based on HCFC 122) was used. The gas stream leaving the reactor contained 92.8% of chlorodifluoroacetyl chloride in addition to 1.0% of 1,1-difluorotetrachloroethane (HCFC 112a) as products. The conversion of HCFC 122 was 94% and the selectivity was 93%.

Example 4

Example 2 was repeated using an apparatus made of Duran-50™ glass. The results corresponded to those of Example 2.

Example 5

Example 3 was repeated using an apparatus made of Duran-50™ glass. The results corresponded to those of Example 3.

Example 6: Continuous preparation of trifluoroacetyl chloride by photochemical oxidation of $CF_3\text{–}CHCl_2$ (HCFC 123) with oxygen through borosilicate glass and with chlorine as a sensitizer.

A mixture of $CF_3\text{–}CHCl_2$ (from a pre-evaporator at T=100° C.) and pure oxygen in a molar ratio of 1:1.2 was metered as a gas together with 38 mole-% of $Cl_2$ (based on HCFC 123) at an internal reactor temperature of 100° C. into a 400 ml immersed shaft photolysis reactor and simultaneously irradiated through Pyrex™ glass using a high-pressure mercury lamp TQ 718 from Heraeus (500 W setting). The rate of addition of HCFC 123 was 0.96 mole/30 min. The gas stream leaving the reactor contained 98.6% of trifluoroacetyl chloride in addition to 1.1% of 1,1,1-trichlorotrifluoroethane (113a) as products. The conversion of HCFC 123 was 71% and the selectivity was 99%.

Example 7

The reaction mixture and procedure corresponded to Example 6, except that 16 mole-% of chlorine gas (based on HCFC 123) and an HCFC 123/$O_2$ molar ratio of 1:1.7 were used. The conversion was 96% and the selectivity was 97%.

Example 8

Example 6 was repeated using an apparatus made of Duran-50™ glass. The results corresponded to those of Example 6.

Example 9

Example 7 was repeated using an apparatus made of Duran-50™ glass. The results corresponded to those of Example 7.

Example 10: Preparation of trifluoroacetyl chloride by photochemical oxidation of $CF_3CHCl_2$ with oxygen through Duran (Pyrex) glass using doped radiators as light sources.

Example 10.1
Radiation source: Gallium iodide-doped high-pressure mercury lamp.

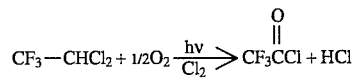

A mixture of $CF_3\text{—}CHCl_2$ (HCFC 123 from a pre-evaporator at T= 100° C.) and pure oxygen in a molar ratio of 1:1.17 was metered as a gas together with 20 mole-% of $Cl_2$ (based on 123) at an internal reactor temperature of 100° C. into a 400 ml immersed shaft photolysis reactor and simultaneously irradiated with an Hg high-pressure radiator TQ 718 Z1 from Heraeus (500 W setting) through Pyrex or Duran 50 glass. The addition rate of 123 was 0.96 mole/30 min. The selectivity by gas chromatography (GC) analysis of the reaction was 100% and the conversion (with adjustment of the lamp power to 500 W) was 45%.

Example 10.2
Radiation source: Thallium iodide-doped high-pressure mercury lamp.

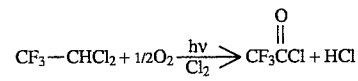

A mixture of $CF_3\text{—}CHCl_2$ (HCFC 123 from a pre-evaporator at T= 100° C.) and pure oxygen in a molar ratio of 1:1.18 was metered as a gas together with 20 mole-% of $Cl_2$ (based on 123) at an internal reactor temperature of 100° C. into a 400 ml immersed shaft photolysis reactor and simultaneously irradiated with a high-pressure mercury lamp TQ 718 Z2 from Heraeus (500 W setting) through Pyrex or Duran 50 glass. The addition rate of 123 was 0.96 mole/30 min. The selectivity of the reaction was 98% and the conversion (with adjustment of the lamp power to 500 W) was 83%.

Example 10.3
Radiation source: Cadmium iodide-doped high-pressure mercury lamp.

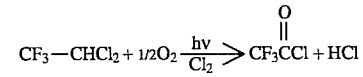

A mixture of $CF_3\text{—}CHCl_2$ (from a pre-evaporator at T=100° C.) and pure oxygen in a molar ratio of 1:1.23 was metered as a gas together with 20 mole-% of $Cl_2$ (based on 123) at an internal reactor temperature of 100° C. into a 400 ml immersed shaft photolysis reactor and simultaneously irradiated with an Hg high-pressure radiator TQ 718 Z3 from Heraeus (500 W setting) through Pyrex or Duran 50 glass. The addition rate of 123 was 0.96 mole/30 min. The selectivity of the reaction was 100% and the conversion (with adjustment of the lamp power to 500 W) was likewise 100%.

It can be seen from Examples 10.1 to 10.3 that despite decreased lamp power, a considerable increase in conversion is observed when using doped light sources.

Example 11: Preparation of trifluoroacetyl chloride using un-doped light sources with decreased lamp power.

Example 10.1 was repeated analogously. This time, however, an un-doped high-pressure mercury lamp TQ 718 from Heraeus was used; the lamp power was 500 W as in Example 10.1. The selectivity was 100% (GC) and the conversion was 41%.

Example 12: Preparation of pentafluoropropionyl chloride by photochemical oxidation of $CF_3CF_2CHCl_2$ (225 ca) with oxygen through Duran glass and with chlorine as a sensitizer.

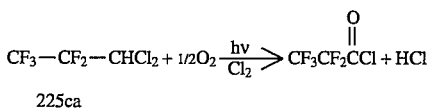
225ca

A mixture of $CF_3CF_2CHCl_2$ (98% purity; from a pre-evaporator at T=130° C.) and pure oxygen in a molar ratio of 1:1.6 was metered as a gas at an internal reactor temperature of 100° C. together with 20 mole-% of $Cl_2$ (based on 225 ca) into a 400 ml immersed shaft photolysis reactor and simultaneously irradiated with a high-pressure mercury lamp TQ 718 from Heraeus (setting 700 W) through Pyrex or Duran 50 glass. The rate of addition of 225 ca was 0.25 mole/15 min. According to a gas chromatogram, the gas stream leaving the reactor contained 96.2% of pentafluoropropionyl chloride, based on the total content of carbon-containing products set to 100%. The selectivity was thus 96.2%, and the conversion was 61.5%.

In all experiments, the reaction product was worked up (separation of chlorine) either by passing the reactor gas stream into alcohol (esterification of the acid chlorides) or by fractional fine distillation (trifluoroacetyl chloride advantageously in a pressure column).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A process for preparing a compound corresponding to the formula

in which R is fluorine or perfluorinated alkyl having 1 to 10 carbon atoms and X is chlorine or fluorine, said process comprising reacting a starting compound corresponding to the formula

in which R and X have the above meanings, with oxygen in the gas phase in the presence of added elemental chlorine and under exposure to activating irradiation with light having a wavelength $\lambda \geq 290$ nm.

2. A process according to claim 1, wherein the reaction is carried out in a flow-through apparatus.

3. A process according to claim 2, wherein starting materials are continuously introduced into the apparatus and reaction product is continuously withdrawn from the apparatus.

4. A process according to claim 2, wherein the average residence time in the flow-through apparatus is between 0.1 and 30 minutes.

5. A process according to claim 1, wherein the process is carried out under unpressurized conditions.

6. A process according to claim 1, wherein the molar ratio between the starting compound of formula $RCFXCHCl_2$ and the elemental chlorine lies in the range from 100:1 to 3:1.

7. A process according to claim 1, wherein the molar ratio between the starting compound of formula $RCFXCHCl_2$ and the oxygen ($O_2$) lies in the range from 1:0.5 to 1:20.

8. A process according to claim 1, wherein the starting compound is 1,1,1-trifluoro-2,2-dichloroethane (HCFC 123) and trifluoroacetyl chloride is produced.

9. A process according to claim 1, wherein the starting compound is 1,1-difluoro-1,2,2-trichloroethane (HCFC 122) and chlorodifluoroacetyl chloride is produced.

10. A process according to claim 1, wherein the starting compound is 1,1,1,2,2-pentafluoro-3,3-dichloropropane (HCFC 225 ca) and pentafluoropropionyl chloride is produced.

11. A process according to claim 1, wherein the reaction is carried out at a temperature of up to 200° C.

12. A process according to claim 11, wherein the reaction is carried out at a temperature in the range from 50° to 130° C.

13. A process according to claim 1, wherein an Hg high-pressure lamp doped with a metal iodide is used as a source for the activating radiation.

14. A process according to claim 13, wherein the source for the activating radiation is a Hg high-pressure lamp doped with gallium iodide, thallium iodide or cadmium iodide.

* * * * *